US006747151B2

(12) United States Patent
Rajagopalan et al.

(10) Patent No.: US 6,747,151 B2
(45) Date of Patent: Jun. 8, 2004

(54) AZO COMPOUNDS FOR TYPE I PHOTOTHERAPY

(75) Inventors: Raghavan Rajagopalan, Solon, OH (US); Gary L. Cantrell, Troy, MO (US); Joseph E. Bugaj, St. Charles, MO (US); Samuel I. Achilefu, St. Louis, MO (US); Richard B. Dorshow, St. Louis, MO (US)

(73) Assignee: Mallinckrodt, Inc., St. Louis, MO (US)

( * ) Notice: Subject to any disclaimer, the term of this patent is extended or adjusted under 35 U.S.C. 154(b) by 0 days.

(21) Appl. No.: 10/272,123

(22) Filed: Oct. 15, 2002

(65) Prior Publication Data

US 2003/0072763 A1 Apr. 17, 2003

Related U.S. Application Data

(63) Continuation-in-part of application No. 09/849,163, filed on May 4, 2001, now Pat. No. 6,485,704.

(51) Int. Cl.$^7$ .................. C07D 237/26; C07D 237/36; C07D 487/00

(52) U.S. Cl. .................. 544/234; 424/1.11; 424/1.65; 424/1.69; 424/1.73; 424/9.6; 548/302.1; 544/224; 544/233

(58) Field of Search .................. 424/1.11, 1.65, 424/1.69, 1.49, 9.8, 1.73, 9.7, 9.3, 9.6; 548/300.1, 301.7, 302.1; 514/2, 9, 23; 530/300; 544/224, 233, 234

(56) References Cited

U.S. PATENT DOCUMENTS

| 5,518,888 | A | 5/1996 | Waldman ............. 435/7.23 |
| 5,714,342 | A | 2/1998 | Komoriya et al. .......... 435/23 |
| 6,485,704 | B1 * | 11/2002 | Rajagopalan et al. ....... 424/9.1 |

OTHER PUBLICATIONS

Lipson et al., *Hematoporphyrin Derivative For Detection And Management Of Cancer*, 1967, Cancer, 20, pp. 2255–2257.
W. Roberts and T. Hasan, *Role of Neovasculature and Vascular Permeability On The Tumor Retention Of Photodynamic Agents*, 1992, Cancer Research, 52, pp. 924–930.
Andreoni et al., *Tumour Photosensitization By Chemotherapeutic Drugs*, 1993, Biologija, Nr 3, pp. 43–46.
Takemura et al., *Mechanism Of Photodynamic Therapy: Exploration By Photophysicochemical Study*, 1993, Frontiers of Photobiology, Shima et al., Editors, pp. 503–506.
M. Hamblin and E. Newman, *On the Mechanism Of The Tumour–Localising Effect In Photodynamic Therapy*, 1994, Journal of Photochemistry and Photobiology, 23, pp. 3–8.
G. Stables and D. Ash, *Photodynamic Therapy*, 1995, Cancer Treatment Reviews, 21, pp. 311–323.

Van Geel et al., *Photosensitizing Efficacy Of MTHPC–PDT Compared To Photofrin–PDT In The RIFI Mouse Tumour And Normal Skin*, 1995, International Journal of Cancer, 60, pp. 388–394.
Ballou et al., *Tumor Labeling In Vivo Using Cyanin–Conjugated Monoclonal Antibodies*, 1995, Cancer Immunology and Immunotherapy, 41, pp. 257–263.
Luo et al., *Rapid Initiation Of Apoptosis By Photodynamic Therapy*, 1996, Photochemistry and Photobiology, 63(4), pp. 528–534.
G. Jori, *Tumour Photosensitizers: Approaches To Enhance The Selectivity And Efficiency Of Photodynamic Therapy*, 1996, Journal of Photochemistry and Photobiology B: Biology, 36, pp. 87–93.
J. Hebden and D. Delpy, *Diagnostic Imaging With Light*, 1997, The British Journal of Radiology, 70, S206–S214.
Dougherty et al., *Photoradiation Therapy II. Cure Of Animal Tumours With Hematoporphyrin And Light*, 1975, Journal of National Cancer Institute, 55, pp. 115–121.
Miller et al., *Preclinical Assessment Of Hypocrellin B and Hypocrellin B Derivatives As Sensitizers For Photodynamic Therapy Of Cancer: Progress Update*, 1997, Photochemistry and Photobiology, 65(4), pp. 714–722.
G. Jori, *Novel Therapeutic Modalities Based On Photosensitized Processes*, 1997, EPA Newsletter, 60, pp. 12–18.
G. Freiherr, *The Light Stuff: Optical Imaging in Medical Diagnosis*, 1998, Medical Devices & Diagnostic Industry, 40–46.
Trauner et al., *Photodynamic Synovectomy Using Benzoporphyrin Derivative In An Antigen–Induced Arthritis Model For Rheumatoid Arthritis*, 1998, Photochemistry and Photobiology, 67(1), pp. 133–139.
Licha et al., *New Contrast Agents For Optical Imaging: Acid–Cleavable Conjugates Of Cyanine Dyes With Biomolecules*, 1999, In Biomedical Imaging: Reporters, Dyes, and Instrumentation, D.J. Bornhop, C. Contag, and E.M. Sevick–Muraca (Eds.), Proceedings of SPIE, 3600, pp. 29–35.
Achilefu et al., *Novel Receptor–Targeted Fluorescent Contrast Agents For In Vivo Tumor Imaging*, 2000, Investigative Radiology, 35(8), pp. 479–485.
Parasassi et al., *Two–Photon Microscopy Of Aorta Fibers Shows Proteolysis Induced By LDL Hydroperoxides*, 2000, Free Radicals In Biology & Medicine, 28(11), pp. 1589–1597.

(List continued on next page.)

Primary Examiner—Dameron L. Jones
(74) Attorney, Agent, or Firm—Wood, Herron & Evans, L.L.P.

(57) ABSTRACT

Novel azo compounds and their bioconjugates for phototherapy and/or photodiagnosis of tumors and other lesions. The azo derivatives of the present invention are designed to absorb at the low-energy ultraviolet, visible, or near-infrared (NIR) region of the electromagnetic spectrum. The phototherapeutic effect is caused by direct interaction of free radicals, the reactive intermediate produced upon photoexcitation of the azo compound, with the tissue of interest.

8 Claims, 2 Drawing Sheets

OTHER PUBLICATIONS

Hnatowich et al., *Radioactive Labeling of Antibody: A Simple and Efficient Method*, 1983, Science, 220, pp. 613–615.

S. Sandler and W. Karo, *Chapter 14 Azo Compounds, in Organic Functional Group Preparations*, 1986, Second Edition, H.H. Wasserman (Ed.), Academic Press, New York, pp. 353–413.

M.D. Daniell and J.S. Hill, *A History Of Photodynamic Therapy*, 1991, Aust. N.Z. Journal of Surgery, 61, pp. 340–348.

M. Korbelik, *Photosensitizers In Photodynamic Therapy*, 1991, Periodicum Biologorum, 93(4), pp. 563–574.

G. Jori and E. Reddi, *Second Generation Photosensitizers For The Photodynamic Therapy Of Tumours*, 1991, Light in Biology and Medicine, 2, R. H. Douglas et al. (Eds.), Plenum Press, New York, pp. 253–266.

G. Jori, *Far–red–absorbing Photosensitizers: Their Use In The Photodynamic Therapy Of Tumours*, 1992, Journal of Photochemistry and Photobiology A: Chemistry, 62, pp. 371–378.

Pelegrin et al., *Photoimmunodiagnosis With Antibody–Fluorescein Conjugates: In Vitro and In Vivo Preclinical Studies*, 1992, Journal of Cellular Pharmacology, 3, pp. 141–145.

* cited by examiner

AZO COMPOUNDS FOR TYPE I PHOTOTHERAPY

This application is a continuation-in-part of U.S. application Ser. No. 09/849,163 filed May 4, 2001, now U.S. Pat. No. 6,485,704 and expressly incorporated by reference herein in its entirety.

FIELD OF THE INVENTION

This invention relates generally to novel azo bioconjugates for use in phototherapy.

BACKGROUND OF THE INVENTION

The use of visible and near-infrared (NIR) light in clinical practice is growing rapidly. Compounds absorbing or emitting in the visible, NIR, or long-wavelength (UV-A, >350 nm) region of the electromagnetic spectrum are potentially useful for optical tomographic imaging, endoscopic visualization, and phototherapy. However, a major advantage of biomedical optics lies in its therapeutic potential. Phototherapy has been demonstrated to be a safe and effective procedure for the treatment of various surface lesions, both external and internal. Its efficacy is comparable to that of radiotherapy, but without the harmful radiotoxicity of critical non-target organs.

Phototherapy has been in existence for many centuries and has been used to treat various skin surface ailments. As early as 1400 B.C. in India, plant extracts (psoralens), in combination with sunlight, were used to treat vitiligo. In 1903, Von Tappeiner and Jesionek used eosin as a photosensitizer for the treatment of skin cancer, lupus of the skin, and condylomata of female genitalia. Over the years, the combination of psoralens and ultraviolet A (low-energy) radiation has been used to treat a wide variety of dermatological diseases including psoriasis, parapsoriasis, cutaneous T-cell lymphoma, eczema, vitiligo, areata, and neonatal bilirubinemia. Although the potential of cancer phototherapy has been recognized since early 1900's, systematic studies to demonstrate safety and efficacy began only in 1967 with the treatment of breast carcinoma. Dougherty et al. subsequently conclusively established that long-term cure is possible with photodynamic therapy (PDT). Currently, phototherapeutic methods are also being investigated for the treatment of some cardiovascular disorders such as atherosclerosis and vascular restenosis for the treatment rheumatoid arthritis, and for the treatment of some inflammatory diseases such as Crohn's disease.

Phototherapeutic procedures require photosensitizers (i.e. chromophores) which have high absorptivity. These compounds should preferably be chemically inert, and become activated only upon irradiation with light of an appropriate wavelength. Light-initiated selective tissue injury can be induced when these photosensitizers bind to target tissues, either directly or through attachment to a bioactive carrier. Furthermore, if the photosensitizer is also a chemotherapeutic agent (e.g. anthracycline antitumor agents), then an enhanced therapeutic effect can be attained.

Effective phototherapeutic agents should have the following properties: (a) large molar extinction coefficient; (b) long triplet lifetime; (c) high yield of singlet oxygen and/or other reactive intermediates, viz., free radicals, nitrenes, carbenes, open-shell ionic species such as cabonium ions and the like; (d) efficient energy or electron transfer to cellular components; (e) low tendency to form aggregation in aqueous milieu; (f) efficient and selective targeting of lesions; (g) rapid clearance from blood and non-target tissues; (h) low systemic toxicity; and (i) lack of mutagenicity.

Photosensitizers operate via two distinct pathways, termed Types 1 and 2. The type 1 mechanism is shown in the following scheme:

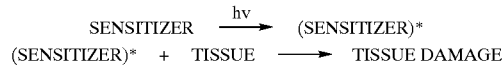

After photoexcitation, the Type 1 mechanism involves direct energy or electron transfer from the photosensitizer to the cellular components, thereby causing cell death. After photoexcitation, the Type 2 mechanism involves distinct steps as shown in the following scheme:

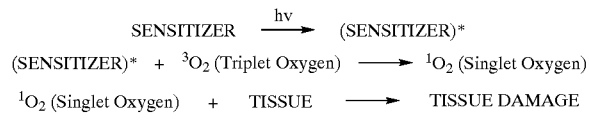

In the first step, singlet oxygen is generated by energy transfer from the triplet excited state of the photosensitizer to the oxygen molecules surrounding the tissues. In the second step, collision of a singlet oxygen with the tissues promotes tissue damage. In both Type 1 and Type 2 mechanisms, the photoreaction proceeds via the lowest triplet state of the sensitizer. Hence, a relatively long triplet lifetime is required for effective phototherapy. In contrast, a relatively short triplet lifetime is required to avoid photodamage to the tissue caused by photosensitizers.

The biological basis of tissue injury brought about by tumor phototherapeutic agents has been the subject of intensive study. Various reasonable biochemical mechanisms for tissue damage have been postulated even though the type and number of photosensitizers employed in these studies are relatively small. These biochemical mechanisms are as follows: a) cancer cells upregulate the expression of low density lipoprotein (LDL) receptors, and PDT agents bind to LDL and albumin selectively; (b) porphyrin-like substances are selectively taken up by proliferative neovasculature; (c) tumors often contain an increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Most of the currently known photosensitizers are commonly referred to as PDT agents and operate via the Type 2 mechanism. For example, Photofrin II, a hematoporphyrin derivative, was approved by the United States Food and Drug Administration for the treatment of bladder, esophageal, and late-stage lung cancers. However, Photofrin II has been shown to have several drawbacks: low molar absorptivity, ($\epsilon$=3000M$^{-1}$), low singlet oxygen quantum yield ($\phi$=0.1), chemical heterogeneity, aggregation, and prolonged cutaneous photosensitivity. Hence, there has been considerable effort in developing safer and more effective photosensitizers for PDT that exhibit improved light absorbance properties, better clearance, and decreased skin photosensitivity compared to those of Photofrin II. These photosensitizers include monomeric porphyrin derivatives, corrins, cyanines, phthalocyanines, phenothiazines, rhodamines, hypocrellins, and the like. However, these phototherapeutic agents also mainly operate via the Type 2 mechanism.

Surprisingly, there has not been much attention directed at developing Type 1 phototherapeutic agents, despite the fact that the Type 1 mechanism seems inherently more efficient than the Type 2 mechanism. First, unlike Type 2, Type 1 photosensitizers do not require oxygen for causing cellular injury. Second, the Type 1 mechanism involves two steps (photoexcitation and direct energy transfer) whereas the Type 2 mechanism involves three steps (photoexcitation, singlet oxygen generation, and energy transfer). Furthermore, some tumors have hypoxic regions that render the Type 2 mechanism ineffective. In spite of the drawbacks associated with the Type 2 mechanism, however, only a small number of compounds have been developed that operate through the Type 1 mechanism, e.g. anthracyline antitumor agents.

Thus, there is a need to develop effective phototherapeutic agents that operate through the Type 1 mechanism. Phototherapeutic efficacy can be further enhanced if the excited state photosensitizers can generate reactive intermediates such as free radicals, nitrenes, carbenes, and the like. These have much longer lifetimes than the excited chromophore and have been shown to cause considerable cell injury.

SUMMARY OF THE INVENTION

The present invention addresses this need and discloses novel azo derivatives and their bioconjugates that absorb in the low-energy, ultraviolet, visible, or near-infrared (NIR) region of the electromagnetic spectrum that are used for the phototherapy of tumors and other lesions. More specifically, the present invention discloses azo compounds having the formula 1

Formula 1

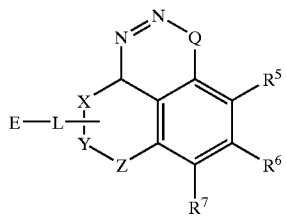

where Q is a single bond or —$CR^1R^2$; $R^1$ and $R^2$ are independently selected from the group consisting of hydrogen, C1–C10 alkyl, C5–C10 aryl, C1–C10 alkoxyalkyl; C1–C10 polyhydroxyalkyl, —$(CH_2)_aCO_2H$, and —$(CH_2)_bNR^3R^4$; $R^3$ and $R^4$ are independently selected from the group consisting of hydrogen, C1–C10 alkyl, C5–C10 aryl, C1–C10 polyhydroxyalkyl, and —$(CH_2)_aCO_2H$; $R^5$, $R^6$, and $R^7$ are independently selected from the group consisting of hydrogen, C1–C10 alkyl, C5–C10 aryl, hydroxyl, —$SO_3H$, C1–C10 alkoxyl, C1–C10 polyhydroxyalkyl, C1–C10 polyalkoxyalkyl, —$(CH_2)_a$ $CO_2H$, and —$(CH_2)_bNR^3R^4$; X is selected from the group consisting of —$CR^8R^9$, —O—, —$NR^3$, —S—, and —C=O; Y is selected from the group consisting of —$CR^{10}R^{11}$, —O—, —$NR^3$, —S—, and —C=O; Z is selected from the group consisting of —$CR^{12}R^{13}$, —O—, —$NR^3$, —S—, and —C=O; $R^8$ to $R^{13}$ are independently selected from the group consisting of hydrogen, C1–C10 alkyl, C5–C10 aryl, C1–C10 alkoxyalkyl, C1–C10 polyhydroxyalkyl, —$(CH_2)_aCO_2H$, and —$(CH_2)_bNR^3R^4$; $R^5$–$R^6$, $R^6$–$R^7$, $R^8$–$R^{10}$, or $R^{10}$–$R^{12}$ together optionally form a six-membered alicyclic or aromatic ring; E is either a hydrogen atom or is selected from the group consisting of antibodies, peptides, peptidomimetics, carbohydrates, glycomimetics, drugs, hormones, or nucleic acids; L is a linker unit selected from the group consisting of —$(CH_2)_c$—, —$(CH_2)_dCONR^3$—, —$N(R^3)CO(CH_2)_d$—, —$OCO(CH_2)_e$—, —$(CH_2)_fCO_2$—, —OCONH—, —$OCO_2$—, —HNCONH—, —HNCSNH—, —HNNHCO—, —$OSO_2$—, —$NR^3(CH_2)_gCONR^4$—, —$CONR^3(CH_2)_hNR^4CO$—, and —$NR^3CO(CH_2)_iCONR^4$; a, b, d to i independently range from 0 to 10, and c ranges from 1 to 10.

The present invention also discloses a method of performing a phototherapeutic or photodiagnostic procedure using the inventive azo compounds and their derivatives. In the method, an effective amount of an azo photosensitizer having the formula 1

Formula 1

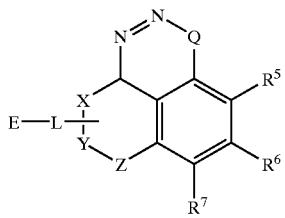

is administered to a subject; where Q is a single bond or —$CR^1R^2$; $R^1$ and $R^2$ are independently selected from the group consisting of hydrogen, C1–C10 alkyl, C5–C10 aryl, C1–C10 alkoxyalkyl, C1–C10 polyhydroxyalkyl, —$(CH_2)_a$ $CO_2H$, and —$(CH_2)_bNR^3R^4$; $R^3$ and $R^4$ are independently selected from the group consisting of hydrogen, C1–C10 alkyl, C5–C10 aryl, C1–C10 polyhydroxyalkyl, and —$(CH_2)_aCO_2H$; $R^5$, $R^6$, and $R^7$ are independently selected from the group consisting of hydrogen, C1–C10 alkyl, C5–C10 aryl, hydroxyl, —$SO_3H$, C1–C10 alkoxyl, C1–C10 polyhydroxyalkyl, C1–C10 polyalkoxyalkyl, —$(CH_2)_a$ $CO_2H$, and —$(CH_2)_bNR^3R^4$; X is selected from the group consisting of —$CR^8R^9$, —O—, —$NR^3$, —S—, and —C=O; Y is selected from the group consisting of —$CR^{10}R^{11}$, —O—, —$NR^3$, —S—, and —C=O; Z is selected from the group consisting of —$CR^{12}R^{13}$, —O—, —$NR^3$, —S—, and —C=O; $R^8$ to $R^{13}$ are independently selected from the group consisting of hydrogen, C1–C10 alkyl, C5–C10 aryl, C1–C10 alkoxyalkyl, C1–C10 polyhydroxyalkyl, —$(CH_2)_aCO_2H$, and —$(CH_2)_bNR^3R^4$; $R^5$–$R^6$, $R^6$–$R^7$, $R^8$–$R^{10}$, or $R^{10}$–$R^{12}$ together optionally form a six-membered ring; E is either a hydrogen atom or is selected from the group consisting of antibodies, peptides, peptidomimetics, carbohydrates, glycomimetics, drugs, hormones, or nucleic acids; L is a linker unit selected from the group consisting of —$(CH_2)_c$—, —$(CH_2)_dCONR^3$—, —$N(R^3)CO(CH_2)_d$—, —$OCO(CH_2)_e$—, —$(CH_2)_fCO_2$—, —OCONH—, —$OCO_2$—, —HNCONH—, —HNCSNH—, —HNNHCO—, —$OSO_2$—, —$NR^3(CH_2)_g$ $CONR^4$—, —$CONR^3(CH_2)_hNR^4CO$—, and —$NR^3CO$ $(CH_2)_iCONR^4$; a, b, d to i independently range from 0 to 10, and c ranges from 1 to 10. The compound is photoactivated and a phototherapeutic or photodiagnostic procedure for tumors, impaired vasculature or other lesions is subsequently performed.

For targeting purposes, external attachment of an epitope is used unless the azo compounds themselves preferentially accumulate in the target tissue. For example, if the photosensitizing chromophore is an anthracycline moiety, it can bind to cancer cells directly and may not require an epitope for targeting purposes.

These and other advantages and embodiments of the inventive compounds and methods will be apparent in view of the following figures, description, and example.

DETAILED DESCRIPTION OF THE INVENTION

Figure 1:
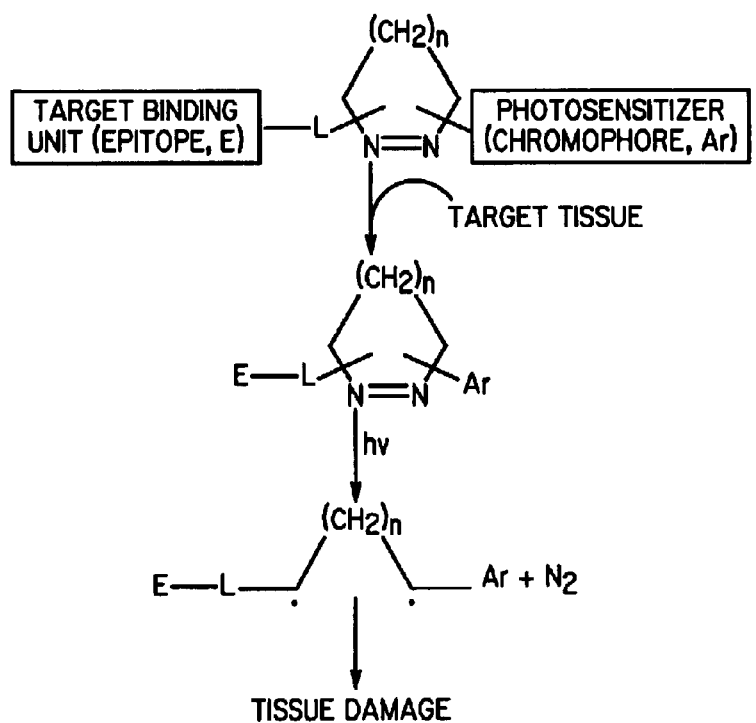
FIG. 1 is a schematic pathway for activation of the inventive compounds.

The present invention discloses novel azo derivatives and their bioconjugates for phototherapy of tumors and other lesions.

Accordingly, the present invention provides new and structurally diverse compositions comprising organic azo compounds of the general formula 1

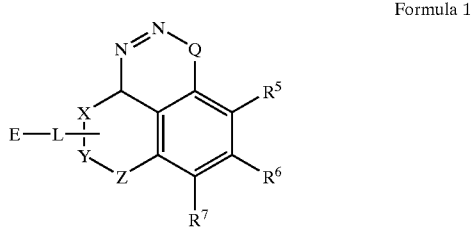

Formula 1 wherein Q is a single bond or —$CR^1R^2$; $R^1$ and $R^2$ are independently selected from the group consisting of hydrogen, C1–C10 alkyl, C5–C10 aryl, C1–C10 alkoxyalkyl, C1–C10 polyhydroxyalkyl, —$(CH_2)_aCO_2H$, and —$(CH_2)_bNR^3R^4$; $R^3$ and $R^4$ are independently selected from the group consisting of hydrogen, C1–C10 alkyl, C5–C10 aryl, C1–C10 polyhydroxyalkyl, and —$(CH_2)_a$ $CO_2H$; $R^5$, $R^6$, and $R^7$ are independently selected from the group consisting of hydrogen, C1–C10 alkyl, C5–C10 aryl, hydroxyl, —$SO_3H$, C1–C10 alkoxyl, C1–C10 polyhydroxyalkyl, C1–C10 polyalkoxyalkyl, —$(CH_2)_a$ $CO_2H$, and —$(CH_2)_bNR^3R^4$; X is selected from the group consisting of —$CR^8R^9$, —O—, —$NR^3$, —S—, and —C=O; Y is selected from the group consisting of —$CR^{10}R^{11}$, —O—, —$NR^3$, —S—, and —C=O; Z is selected from the group consisting of —$CR^{12}R^{13}$, —O—, —$NR^3$, —S—, and —C=O; $R^8$ to $R^{13}$ are independently selected from the group consisting of hydrogen, C1–C10 alkyl, C5–C10 aryl, C1–C10 alkoxyalkyl, C1–C10 polyhydroxyalkyl, —$(CH_2)_aCO_2H$, and —$(CH_2)_bNR^3R^4$; $R^5$–$R^6$, $R^6$–$R^7$, $R^8$–$R^{10}$, or $R^{10}$–$R^{12}$ together optionally form a six-membered ring; E is either a hydrogen atom or is selected from the group comprising antibodies, peptides, peptidomimetics, carbohydrates, glycomimetics, drugs, hormones, or nucleic acids; L is a linker unit selected from the group comprising —$(CH_2)_c$—, —$(CH_2)_dCONR^3$—, —$N(R^3)CO(CH_2)_d$—, —$OCO(CH_2)_e$—, —$(CH_2)_fCO_2$—, —OCONH—, —$OCO_2$—, —HNCONH—, —HNCSNH—, —HNNHCO—, —$OSO_2$—, —$NR^3(CH_2)_2$ $CONR^4$—, —$CONR^3(CH_2)_hNR^4CO$—, and —$NR^3CO$ $(CH_2)_iCONR^4$; a,b, d to i independently range from 0 to 10, and c ranges from 1 to 10.

In one embodiment, azo compounds according to the present invention have the general formula 1 wherein Q is —$CR^1R^2$; $R^1$ and $R^2$ are independently selected from the group consisting of hydrogen, C1–C10 alkyl, C5–C10 aryl, and —$(CH_2)_aCO_2H$; $R^5$, $R^6$, and $R^7$ are independently selected from the group consisting of hydrogen, C1–C10 alkyl, hydroxyl, —$SO_3H$, C1–C10 alkoxyl, and —$(CH_2)_a$ $CO_2H$; X is selected from the group consisting of —$CR^8R^9$, —O—, —$NR^3$, and —C=O; Y is selected from the group consisting of —$CR^{10}R^{11}$, —O—, —$NR^3$, and —C=O; Z is selected from the group consisting of —$CR^{12}R^{13}$, —O—, —$NR^3$, and —C=O; $R^8$ to $R^{13}$ are independently selected from the group consisting of hydrogen, C1–C10 alkyl, C5–C10 aryl, and —$(CH_2)_aCO_2H$; $R^8$ and $R^{10}$ together optionally form a six-membered ring; E is selected from the group consisting of somatostatin receptor binding molecules, heat-sensitive bacterioendotoxin (ST) receptor binding molecules, neurotensin receptor binding molecules, bombesin receptor binding molecules, cholecystekinen (CCK) receptor binding molecule, steroid receptor binding molecules, and carbohydrate receptor binding molecules; L is a linker unit selected from the group consisting of —$(CH_2)_dCONR^3$—, —$N(R^3)CO(CH_2)_d$—, —HNCONH—, —HNCSNH—, and —$NR^3CO(CH_2)_i$ $CONR^4$; and a to i independently range from 0 to 6.

In another embodiment, azo compounds according to the invention having the general formula 1 above wherein Q is —$CR^1R^2$; $R^1$ and $R^2$ are independently selected from the group consisting of hydrogen and C1–C10 alkyl; $R^5$, $R^6$, and $R^7$ are independently selected from the group consisting of hydrogen, hydroxyl, —$SO_3H$, and —$(CH_2)_aCO_2H$; X is selected from the group consisting of —$CR^8R^9$ and —C=O; Y is selected from the group consisting of —$CR^{10}R^{11}$, —$NR^3$, and —C=O; Z is selected from the group consisting of —$CR^{12}R^{13}$, —O—, —$NR^3$, and —C=O; $R^8$ to $R^{13}$ are independently selected from the group consisting of hydrogen, C1–C10 alkyl, C5–C10 aryl, and —$(CH_2)_aCO_2H$; $R^8$ and $R^{10}$ together optionally form a six-membered ring; E is selected from the group consisting of somatostatin receptor binding molecules, ST receptor binding molecules, neurotensin receptor binding molecules, bombesin receptor binding molecules, CCK receptor binding molecule, steroid receptor binding molecules, and carbohydrate receptor binding molecules; L is a linker unit selected from the group consisting of —$N(R^3)CO(CH_2)_d$—, —$(CH_2)_dCONR^3$—, and $NR^3CO(CH_2)_iCONR^4$; and a, b, d, e, f, g, h and i independently range from 0 to 6.

In an additional embodiment, azo compounds according to the invention having the general formula 1 wherein Q is a single bond or —$CR^1R^2$; $R^1$ and $R^2$ are independently selected from the group consisting of hydrogen, C1–C10 alkyl, C5–C10 aryl, C1–C10 alkoxyalkyl, C1–C10 polyhydroxyalkyl, —$(CH_2)_aCO_2H$, and —$(CH_2)_bNR^3R^4$; $R^3$ and $R^4$ are independently selected from the group consisting of hydrogen, C1–C10 alkyl, C5–C10 aryl, C1–C10 polyhydroxyalkyl, and —$(CH_2)_aCO_2H$; $R^5$, $R^6$, and $R^7$ are independently selected from the group consisting of hydrogen, C1–C10 alkyl, C5–C10 aryl, hydroxyl, —$SO_3H$, C1–C10 alkoxyl, C1–C10 polyhydroxyalkyl, C1–C10 polyalkoxyalkyl, —$(CH_2)_aCO_2H$, and —$(CH_2)_bNR^3R^4$; X is selected from the group consisting of —$CR_8R^9$, —O—, —$NR^3$, —S—, and —C=O; Y is selected from the group consisting of —$CR^{10}R^{11}$, —O—, —$NR^3$, —S—, and —C=O; Z is selected from the group consisting of —$CR^{12}R^{13}$, —O—, —$NR^3$, —S—, and —C=O; $R^8$ to $R^{13}$ are independently selected from the group consisting of hydrogen, C1–C10 alkyl, C5–C10 aryl, C1–C10 alkoxyalkyl, C1–C10 polyhydroxyalkyl, —(CH$_2$)$_a$CO$_2$H, and —(CH$_2$)$_b$NR$^3$R$^4$; R$^5$–R$^6$, R$^6$–R$^7$, R$^8$–R$^{10}$, or R$^{10}$–R$^{12}$ together optionally form a six-membered ring; E is either a hydrogen atom or is selected from the group comprising antibodies, peptides, peptidomimetics, carbohydrates, glycomimetics, drugs, hormones, or nucleic acids; L is the linker unit —(CH$_2$)$_c$—, a and b independently range from 0 to 10, and c ranges from 1 to 10.

The inventive compounds operate through the Type 1 mechanism as shown in FIG. 1 wherein —N=N— is the azo moiety that undergoes nitrogen extrusion upon photoactivation, thereby producing free radicals. Ar is an aromatic chromophore that undergoes photosensitization. Aliphatic azo compounds can also be used for phototherapy, but may require high-energy light for activation. L is the linker between the chromophore and the epitope. Epitope (E) is a particular region of the molecule that is recognized by and binds to the target surface. An epitope is usually, but not always, associated with biomolecules. Biomolecules include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Specific examples of biomolecules include steroid hormones for the treatment of breast and prostate lesions; somatostatin, bombesin, CCK, and neurotensin receptor binding molecules for the treatment of neuroendocrine tumors; CCK receptor binding molecules for the treatment of lung cancer; ST receptor and carcinoembryonic antigen (CEA) binding molecules for the treatment of colorectal cancer; dihyroxy-indolecarboxylic acid and other melanin producing biosynthetic intermediates for the treatment of melanoma; integrin receptor and atherosclerotic plaque binding molecules for the treatment of vascular diseases; and amyloid plaque binding molecules for the treatment of brain lesions. Examples of synthetic polymers include polyaminoacids, polyols, polyamines, polyacids, oligonucleotides, aborols, dendrimers, and aptamers.

Coupling of a photodiagnostic and/or phototherapeutic agent to biomolecules can be accomplished by methods well known in the art, as disclosed in Hnatowich et al., *Radiolabeling of Antibodies: A simple and efficient method, Science*, 1983, 220, p. 613; Pelegrin et al., *Photoimmunodiagnostics with antibody-fluorescein conjugates: in vitro and in vivo preclinical studies, Journal of Cellular Pharmacology*, 1992, 3, pp. 141–145; and U.S. Pat. No. 5,714,342, each of which is expressly incorporated by reference herein in its entirety. Successful specific targeting of fluorescent dyes to tumors using antibodies and peptides for diagnostic imaging of tumors has been demonstrated by us and others as described in Achilefu et al., *Novel receptor-targeted fluorescent contrast agents for in vivo imaging of tumors, Investigative Radiology*, 2000, 35, pp. 479–485; Ballou et al., *Tumor labeling in vivo using cyanine conjugated monoclonol antibodies, Cancer Immunology and Immunotherapy*, 1995, 41, pp. 257–263; and Licha et al., *New contrast agent for optical imaging: acid cleavable conjugates of cyanine dyes with biomolecules, in Biomedical Imaging: Reporters, Dyes and Instrumentation. Proceedings of SPIE*, 1999, 3600, pp. 29–35, each of which is expressly incorporated by reference herein in its entirety. Therefore, receptor-targeted phototherapeutic agents of the present invention should be effective in the treatment of various lesions.

In the process outlined in FIG. 1, photoexcitation of the aromatic chromophore effects rapid intramolecular energy transfer to the azo group, resulting in N—C bond rupture with concomitant extrusion of molecular nitrogen and formation of diradicals. The diradicals can also combine with each other to form neutral molecules, provided that their spatial orientation is optimal. The nitrogen that is released could be in a vibrationally excited state and may cause additional cellular injury. This process is very similar to the process observed with azides. For targeting purposes, an external attachment of an epitope is usually required unless the azo compounds themselves preferentially accumulate in the target tissue, thereby obviating the need for an additional binding group. For example, if the Ar moiety is an anthracycline moiety, it can bind to cancer cells directly and may not require an epitope for targeting purposes.

The synthesis of azo compounds is accomplished by a variety of methods well known in the art, as disclosed in Sandier and Karo, *Azo Compounds, Organic Functional Group Preparations*, 1986, Academic Press: New York, pp. 353–409, which is expressly incorporated by reference herein in its entirety. The azo derivatives of the invention contain additional functionalities that can be used to attach various types of biomolecules, synthetic polymers, and organized aggregates for selective delivery to various organs or tissues of interest. Preparations of representative compounds from the embodiments are shown in FIGS. 2–4.

Figure 2:
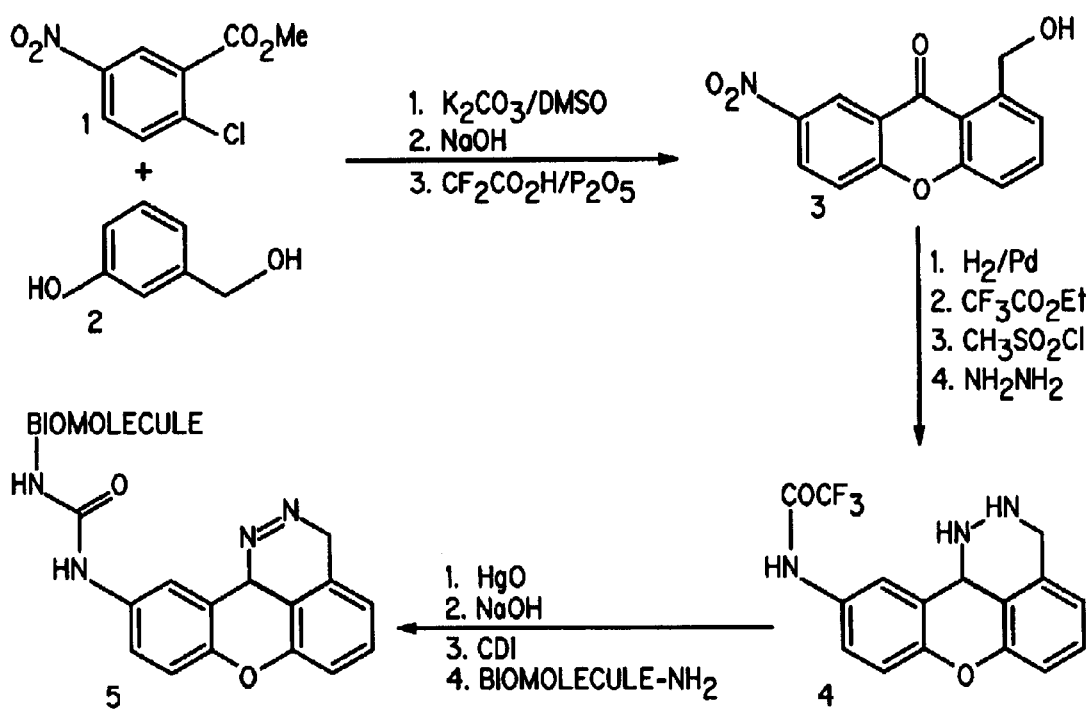
FIG. 2 is a schematic pathway for the synthesis of a cyclic azoxanthene derivative.

FIG. 2 shows a typical preparation of a cyclic azoxanthene derivative 5. Methyl 2-chloro-5-nitrobenzoate 1 is reacted with 3-hydroxybenzyl alcohol 2 and thereafter saponified and cyclized to the nitroxanthone 3. The xanthone 3 is then converted to the azo precursor 4 in four standard steps. The hydrazino derivative 4 is then oxidized with either mercuric oxide or lead tetraacetate and then conjugated to any desired biomolecule of interest using bifunctional coupling reagents such as phosgene, thiophosgene, carbonyldiimidazole, disuccinimidyl carbonate, and the like. Specifically, the biomolecule of the invention pertains to those binding to colorectal, cervical, ovarian, lung, and neuroendocrine tumors. These include somatostatin, cholesystekinin (CCK), bombesin, neuroendrocrine, and heat sensitive bacterioendotoxin (ST) receptor binding compounds.

Figure 3:
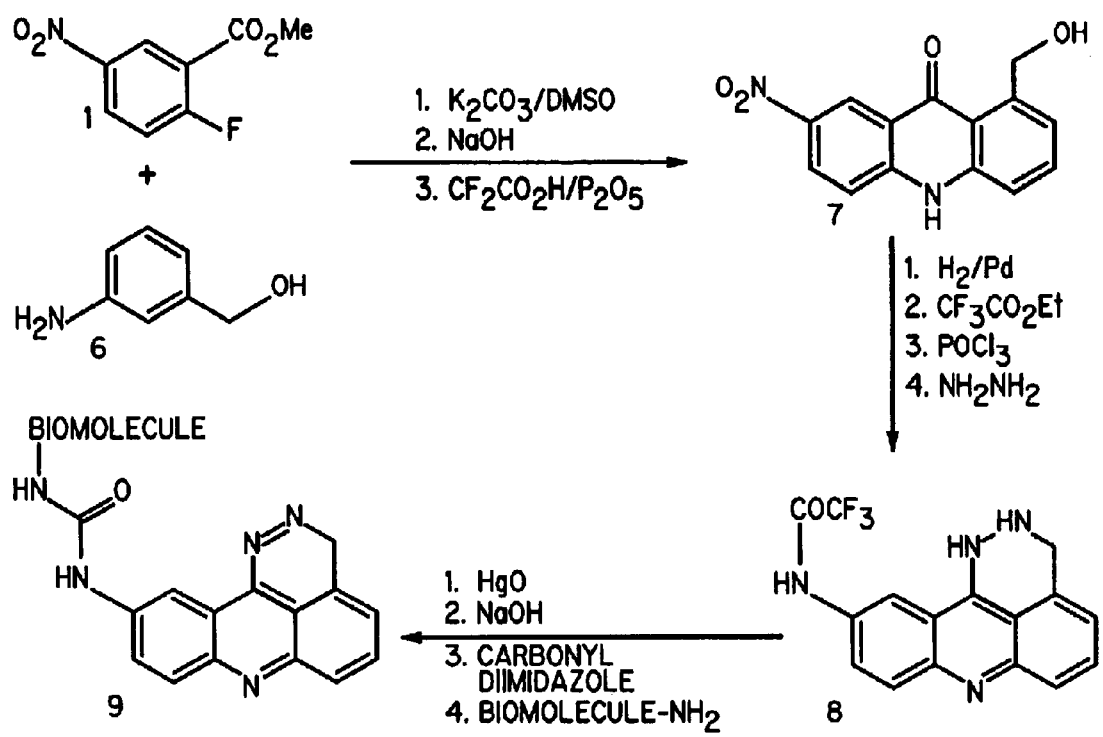
FIG. 3 is a schematic pathway for the synthesis of an azoacridine derivative.

With reference to FIG. 3, the azoacridine derivative 9 can be prepared in a similar manner to the cyclic azoxanthene derivative whose synthetic scheme is shown in FIG. 2. Methyl 2-chloro-5-nitrobenzoate 1 is reacted with 3-hydroxybenzyl amine 6 and thereafter saponified and cyclized to the nitroacridone 7. The acridone 7 is then converted to the azo precursor 8 in four standard steps. The hydrazino derivative 8 is then oxidized with either mercuric oxide or lead tetraacetate and then conjugated to a biomolecule, as previously described, using bifunctional coupling reagents such as disuccinimidyl carbonate, disuccinimidyl oxalate, phosgene, thiophosgene, carbonyidiimidazole and the like.

Figure 4:
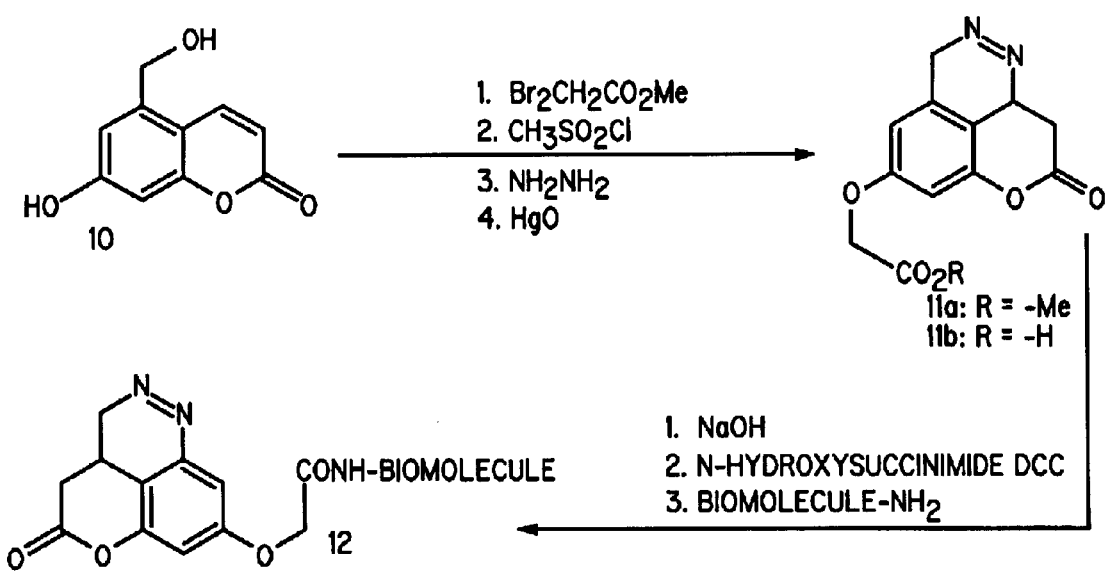
FIG. 4 is a schematic pathway for the synthesis of an azocoumarin derivative.

With reference to FIG. 4, a typical preparation of an azocoumarin derivative 12 is shown. The phenol 10 is first alkylated with methyl bromoacetate and then transformed to the azo compound 11 by standard methods. The ester 11 is saponified and conjugated to the biomolecule using the known bifunctional coupling reagents previously described, or can be conjugated directly using automated peptide synthesis methods as is known to one of skill in the art.

The novel compositions of the present invention may vary widely depending on the contemplated application. For tumors, the biomolecule is selected from the class of tumor markers including, but not limited to, somatostatin, bombesin, neurotensin, CCK, ST, estrogen, and progesterone receptor binding compounds. For vascular lesions, the biomolecule may be selected from the class of integrins, selecting, vascular endothelial growth factor, fibrins, tissue plasminogen activator, thrombin, low density lipoprotein (LDL), high density lipoprotein (HDL), Sialyl Lewis$^x$ and its mimics, and atherosclerotic plaque binding compounds.

As previously described, some compounds accumulate in tumors or other lesions without the assistance of a bioactive carrier. Administration of delta-aminolevulinic acid, an intermediate in porphyrin biosynthesis, results in a two-fold uptake of porphyrins in tumors compared to normal tissues. Similarly, administration of dihydroxyindole-2-carboxylic acid, an intermediate in melanin biosynthesis, produces substantially enhanced levels of melanin in melanoma cells compared to normal cells. Thus, a photosensitizer may be delivered to the site of lesion by attaching it to these types of biosynthetic intermediates.

Methods of performing therapeutic procedures with compositions of the invention are also disclosed. The method encompasses administering to a patient an effective amount of the compositions of the invention contained in a pharmaceutically acceptable formulation. Thereafter, the photosensitizer is allowed to accumulate in the region of interest, followed by illumination with light of wavelength 300 to 1200 nm, preferably 350 to 850 nm, at the site of the lesion. If the lesion is on the skin surface, it can be directly illuminated; otherwise, endoscopic catheters equipped with a light source may be employed to achieve a phototherapeutic effect. The intensity, power, duration of illumination, and the wavelength of the light may vary widely depending on the location and site of the lesions. The fluence rate is preferably, but not always, kept below 200 mW/cm$^2$ to minimize thermal effects. Appropriate power depends on the size, depth, and pathology of the lesion. The inventive compositions have broad clinical utility which includes, but is not limited to, phototherapy of tumors, inflammatory processes, and impaired vasculature.

The inventive compositions can be formulated into photodiagnostic or phototherapeutic compositions for enteral (oral or rectal), parenteral, topical, or cutaneous administration. Topical or cutaneous delivery of the photosensitizer may also include aerosols, creams, gels, solutions, etc. The compositions are administered in doses effective to achieve the desired diagnostic or therapeutic objective. Such doses may vary widely depending upon the particular complex employed, the organs or tissues to be examined, the equipment employed in the clinical procedure, the efficacy of the treatment achieved, and the like. These compositions contain an effective amount of the phototherapeutic agent along with conventional pharmaceutical carriers and excipients appropriate for the type of administration contemplated. These compositions may also include stabilizing agents and skin penetration enhancing agents and also may contain pharmaceutically acceptable buffers, emulsifiers, surfactants, and, optionally, electrolytes such as sodium chloride.

Formulations for enteral administration may vary widely as is well known in the art. In general, such formulations are liquids, which include an effective amount of the composition in an aqueous solution or suspension. Such enteral compositions may optionally include buffers, surfactants, emulsifiers, thixotropic agents, and the like. Compositions for oral administration may also contain flavoring agents and other ingredients for enhancing their organoleptic qualities. A topical application can be formulated as a liquid solution, water/oil emulsion, or suspension of particles, depending on the particular nature of the agent and the type of tissue to be targeted. If the azo compound is water soluble, for instance, a solution in water may be applied to or into the target tissue. The delivery of the azo compounds into and through the skin may be enhanced by using well known methods and agents such as transdermal permeation enhancers, for example, "azone", N-alkylcyclic amides, dimethylsulfoxide, long-chained aliphatic acids (C10), etc. If the azo compound is not water soluble, it may be dissolved in a biocompatible oil (soybean oil, fish oil, vitamin E, linseed oil, vegetable oil, glyceride esters, long-chained fatty esters, etc.) and emulsified with surface-active compounds (vegetable or animal phospholipids; lecithin; long-chained fatty salts and alcohols; Pluronics: polyethylene glycol esters and ethers; etc.) in water to make a topical cream, suspension, water/oil emulsion, water/oil microemulsion, or liposomal suspension to be delivered or applied to the target region. In the case of liposomes, the azo compound may be attached to or be contained in the lamellar material.

The dose of the photosensitizer may vary from about 0.1 mg/kg body weight to about 500 mg/kg body weight. In one embodiment, the dose is in the range of about 0.5 to 2 mg/kg body weight. As one example, for compositions administered parenterally, a sterile aqueous solution or suspension of the photosensitizer may be present in a concentration ranging from about 1 nM to about 0.5 M, typically in a concentration from about 1 $\mu$M to about 10 mM.

In general, a formulated azo compound is administered at a dose or in a concentration which is effective, upon exposure to light, to partially or completely inactivate a target tissue within a biological medium. The biological medium is exposed for a period of time to light of a wavelength that is effective to activate the dye which produces type I destruction in the target tissue. The concentration of the azo compound at the target tissue is the outcome of either passive or active uptake processes in the tissue. An example of passive uptake would be where the azo compound is attached or is contained within a particulate carrier. If the carrier is of an appropriate size, in the range of about 100 nm to about 1000 nm, it will "leak" into the perfusion boundary of vascular tumors. An example of active uptake would be where a receptor based attachment binds a particular receptor that is expressed on the target tissue. The effective concentration of the azo compound is thus dependent on the nature of the formulation, method of delivery, target tissue, activation method and toxicity of the azo to the surrounding normal tissue.

The following example illustrates a specific embodiment of the invention pertaining to the preparation and properties of a typical bioconjugate derived from bombesin, a bioactive peptide, and a phototherapeutic molecule, the azocoumarin derivative 11b as shown in FIG. 4.

EXAMPLE
Synthesis of azocoumarin-bombesin (7–14) conjugate

The peptide is prepared by fluorenylmethoxycarbonyl (Fmoc) solid phase peptide synthesis strategy with a commercial peptide synthesizer from Applied Biosystems (Model 432A SYNERGY Peptide Synthesizer). The first peptide cartridge containes Wang resin pre-loaded with an amide resin on 25-$\mu$mole scale. The amino acid cartridges are placed on the peptide synthesizer and the product is synthesized from the C- to the N-terminal position.

Coupling of the Fmoc-protected amino acids (75 $\mu$mol) to the resin-bound free terminal amine (25 $\mu$mol) is carried out with 2-(1H-benzotriazol-1-yl)-1,1,3,3-tetramethyluronium hexafluorophosphate (HBTU, 75 $\mu$mol)/N- hydroxybenzotriazole (HOBt, 75 μmol). Each Fmoc protecting group on the solid support is removed with 20% piperidine in dimethylformamide before a subsequent amino acid is coupled to it. The last cartridge contains the azo compound 11b as shown in FIG. 4, which is coupled to the peptide automatically, thus avoiding the need for post-synthetic manipulations.

After the synthesis is completed, the product is cleaved from the solid support with a cleavage mixture containing trifluoroacetic acid (85%):water (5%):phenol (5%):thioanisole (5%) for six hours. The peptide-azide conjugate is precipitated with t-butyl methyl ether and lyophilized in water/acetonitrile (2:3) mixture. The conjugate is purified by high performance liquid chromatography (HPLC) and analyzed with liquid chromatography/mass spectroscopy (LC/MS).

It should be understood that the embodiments of the present invention shown and described in the specification are only specific embodiments of the inventors who are skilled in the art and are not limiting in any way. Therefore, various changes, modifications or alterations to those embodiments may be made or resorted to without departing from the spirit of the invention and the scope of the following claims. For example, the compounds containing polycyclic aromatic chromophores can also be used for optical diagnostic imaging purposes.

What is claimed is:

1. A compound of formula

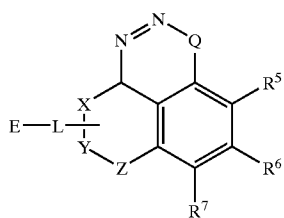

Formula 1 wherein Q is a single bond or —CR$^1$R$^2$; R$^1$ and R$^2$ are independently selected from the group consisting of hydrogen, C1–C10 alkyl, C5–C10 aryl, C1–C10 alkoxyalkyl, C1–C10 polyhydroxyalkyl, —(CH$_2$)$_a$CO$_2$H, and —(CH$_2$)$_b$NR$^3$R$^4$; R$^3$ and R$^4$ are independently selected from the group consisting of hydrogen, C1–C10 alkyl, C5–C10 aryl, C1–C10 polyhydroxyalkyl, and —(CH$_2$)$_a$CO$_2$H; R$^5$, R$^6$, and R$^7$ are independently selected from the group consisting of hydrogen, C1–C10 alkyl, C5–C10 aryl, hydroxyl, —SO$_3$H, C1–C10 alkoxyl, C1–C10 polyhydroxyalkyl, C1–C10 polyalkoxyalkyl, —(CH$_2$)$_a$CO$_2$H, and —(CH$_2$)$_b$NR$^3$R$^4$; X is selected from the group consisting of —CR$^8$R$^9$, —O—, —NR$^3$, —S—, and —C=O; Y is selected from the group consisting of —CR$^{10}$R$^{11}$, —O—, —NR$^3$, —S—, and —C=O; Z is selected from the group consisting of —CR$^{12}$R$^{13}$, —O—, —NR$^3$, —S—, and —C=O; R$^8$ to R$^{13}$ are independently selected from the group consisting of hydrogen, C1–C10 alkyl, C5–C10 aryl, C1–C10 alkoxyalkyl, C1–C10 polyhydroxyalkyl, —(CH$_2$)$_a$CO$_2$H, and —(CH$_2$)$_b$NR$^3$R$^4$; R$^5$–R$^6$, R$^6$–R$^7$, R$^8$–R$^{10}$, or R$^{10}$–R$^{12}$ together optionally form a six-membered ring; E is either a hydrogen atom or is selected from the group comprising antibodies, peptides, peptidomimetics, carbohydrates, glycomimetics, drugs, hormones, or nucleic acids; L is the linker unit —(CH$_2$)$_c$—, a and b independently range from 0 to 10, and c ranges from 1 to 10.

2. The compound of claim 1, wherein Q is —CR$^1$R$^2$; R$^1$ and R$^2$ are independently selected from the group consisting of hydrogen and C1–C10 alkyl; R$^5$, R$^6$, and R$^7$ are independently selected from the group consisting of hydrogen, hydroxyl, —SO$_3$H, and —(CH$_2$)$_a$CO$_2$H; X is —C=O; Y is —CR$^{10}$R$^{11}$; Z is —CR$^{12}$R$^{13}$; R$^{10}$ to R$^{13}$ are independently selected from the group consisting of hydrogen, C1–C10 alkyl, C5–C10 aryl, and —(CH$_2$)$_a$CO$_2$H; E is selected from the group consisting of somatostatin receptor binding molecules, heat-sensitive bacterioendotoxin (ST) receptor binding molecules, neurotensin receptor binding molecules, bombesin receptor binding molecules, cholecystekinen (CCK) receptor binding molecule, steroid receptor binding molecules, and carbohydrate receptor binding molecules; and a independently ranges from 0 to 6.

3. The compound of claim 1, wherein Q is —CR$^1$R$^2$; R$^1$ and R$^2$ are independently selected from the group consisting of hydrogen and C1–C10 alkyl; R$^5$, R$^6$, and R$^7$ are independently selected from the group consisting of hydrogen, hydroxyl, —SO$_3$H, and —(CH$_2$)$_a$CO$_2$H; X is —CR$^8$R$^9$; Y is —C=O; Z is selected from the group consisting of —CR$^{12}$R$^{13}$, —O—, and —NR$^3$; R$^8$, R$^9$, R$^{12}$ and R$^{13}$ are independently selected from the group consisting of hydrogen, C1–C10 alkyl, C5–C10 aryl, and —(CH$_2$)$_a$CO$_2$H; E is selected from the group consisting of somatostatin receptor binding molecules, ST receptor binding molecules, neurotensin receptor binding molecules, bombesin receptor binding molecules, CCK receptor binding molecule, steroid receptor binding molecules, and carbohydrate receptor binding molecules; and a independently ranges from 0 to 6.

4. The compound of claim 1, wherein Q is —CR$^1$R$^2$; R$^1$ and R$^2$ are independently selected from the group consisting of hydrogen and C1–C10 alkyl; R$^5$, R$^6$, and R$^7$ are independently selected from the group consisting of hydrogen, hydroxyl, —SO$_3$H, and —(CH$_2$)$_a$CO$_2$H; X is —CR$^8$R$^9$; Y is selected from the group consisting of —CR$^{10}$R$^{11}$, —O—, and —NR$^3$; Z is —C=O; R$^8$ to R$^{11}$ are independently selected from the group consisting of hydrogen, C1–C10 alkyl, C5–C10 aryl, and —(CH$_2$)$_a$CO$_2$H; E is selected from the group consisting of somatostatin receptor binding molecules, ST receptor binding molecules, neurotensin receptor binding molecules, bombesin receptor binding molecules, CCK receptor binding molecule, steroid receptor binding molecules, and carbohydrate receptor binding molecules; and a independently ranges from 0 to 6.

5. The compound of claim 1, wherein Q is —CR$^1$R$^2$; R$^1$ and R$^2$ are independently selected from the group consisting of hydrogen and C1–C10 alkyl; R$^5$, R$^6$, and R$^7$ are independently selected from the group consisting of hydrogen, hydroxyl, —SO$_3$H, and —(CH$_2$)$_a$CO$_2$H; X is —CR$^8$R$^9$; Y is —CR$^{10}$R$^{11}$; Z is —CR$^{12}$R$^{13}$; R$^8$ and R$^{10}$ together form a benzene ring; R$^9$ and R$^{11}$ are radicals that form carbon-carbon bond; R$^{12}$ and R$^{13}$ are independently selected from the group consisting of hydrogen, C1–C10 alkyl, C5–C10 aryl, and —(CH$_2$)$_a$CO$_2$H; E is selected from the group consisting of somatostatin receptor binding molecules, ST receptor binding molecules, neurotensin receptor binding molecules, bombesin receptor binding molecules, CCK receptor binding molecule, steroid receptor binding molecules, and carbohydrate receptor binding molecules; and a independently ranges from 0 to 6.

6. The compound of claim 1, wherein Q is —CR$^1$R$^2$; R$^1$ and R$^2$ are independently selected from the group consisting of hydrogen and C1–C10 alkyl; R$^5$, R$^6$, and R$^7$ are independently selected from the group consisting of hydrogen, hydroxyl, —SO$_3$H, and —(CH$_2$)$_a$CO$_2$H; X is —CR$^8$R$^9$; Y is —CR$^{10}$R$^{11}$; Z is —O—; R$^8$ and R$^{10}$ together form a benzene ring; R$^9$ and R$^{11}$ are radicals that form carbon-carbon bond, R$^{12}$ and R$^{13}$ are independently selected from the group consisting of hydrogen, C1–C10 alkyl, C5–C10 aryl, and —(CH$_2$)$_a$CO$_2$H; E is selected from the group consisting of somatostatin receptor binding molecules, ST receptor binding molecules, neurotensin receptor binding molecules, bombesin receptor binding molecules, CCK receptor binding molecule, steroid receptor binding molecules, and carbohydrate receptor binding molecules; and a independently ranges from 0 to 6.

7. The compound of claim 1, wherein Q is —CR$^1$R$^2$; R$^1$ and R$^2$ are independently selected from the group consisting of hydrogen and C1–C10 alkyl; R$^5$, R$^6$, and R$^7$ are independently selected from the group consisting of hydrogen, hydroxyl, —SO$_3$H, and —(CH$_2$)$_a$CO$_2$H; X is —CR$^8$R$^9$; Y is —CR$^{10}$R$^{11}$; Z is —NR$^3$; R$^8$ and R$^{10}$ together form a benzene ring; R$^9$ and R$^{11}$ are radicals that form carbon-carbon bond; R$^{12}$ and R$^{13}$ are independently selected from the group consisting of hydrogen, C1–C10 alkyl, C5–C10 aryl, and —(CH$_2$)$_a$CO$_2$H; E is selected from the group consisting of somatostatin receptor binding molecules, ST receptor binding molecules, neurotensin receptor binding molecules, bombesin receptor binding molecules, CCK receptor binding molecule, steroid receptor binding molecules, and carbohydrate receptor binding molecules; and a independently ranges from 0 to 6.

8. The compound of claim 1, wherein Q is —CR$^1$R$^2$; R$^1$ and R$^2$ are independently selected from the group consisting of hydrogen and C1–C10 alkyl; R$^5$, R$^6$, and R$^7$ are independently selected from the group consisting of hydrogen, hydroxyl, —SO$_3$H, and —(CH$_2$)$_a$CO$_2$H; X is —CR$^8$R$^9$; Y is —CR$^{10}$R$^{11}$; Z is —C=O; R$^8$ and R$^{10}$ together form a benzene ring; R$^9$ and R$^{11}$ are radicals that form carbon-carbon bond; R$^{12}$ and R$^{13}$ are independently selected from the group consisting of hydrogen, C1–C10 alkyl, C5–C10 aryl, and —(CH$_2$)$_a$CO$_2$H; E is selected from the group consisting of somatostatin receptor binding molecules, ST receptor binding molecules, neurotensin receptor binding molecules, bombesin receptor binding molecules, CCK receptor binding molecule, steroid receptor binding molecules, and carbohydrate receptor binding molecules; and a independently ranges from 0 to 6.

\* \* \* \* \*

UNITED STATES PATENT AND TRADEMARK OFFICE
CERTIFICATE OF CORRECTION

PATENT NO. : 6,747,151 B2
DATED : June 8, 2004
INVENTOR(S) : Rajagopalan et al.

It is certified that error appears in the above-identified patent and that said Letters Patent is hereby corrected as shown below:

Column 4,
Line 55, change "$(CH_2),CO_2-$ ," to -- $-(CH_2),CO_2-$ , --.

Column 5,
Line 66, change "$-NR^3(CH_2)_2CONR^4-$," to -- $-NR^3(CH_2)_gCONR^4-$, --.

Column 6,
Line 63, change "$-CR_8R^9$," to -- $-CR^8R^9$, --.

Column 8,
Line 19, change "Sandier and Karo," to -- Sandler and Karo, --.

Column 9,
Line 5, change "integrins, selecting," to -- integrins, selectins, --.

Column 12,
Line 22, change "$-(CH_2)_8CO_2H$;" to -- $-(CH_2)_aCO_2H$; --.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,747,151 B2
DATED : June 8, 2004
INVENTOR(S) : Rajagopalan et al.

It is certified that error appears in the above-identified patent and that said Letters Patent is hereby corrected as shown below:

Column 11,
Line 11, "peptide-azide" should be -- peptide-azo --.

Signed and Sealed this

Twenty-seventh Day of September, 2005

JON W. DUDAS
*Director of the United States Patent and Trademark Office*